United States Patent [19]
Bouchon et al.

[11] Patent Number: 5,507,822
[45] Date of Patent: Apr. 16, 1996

[54] BALL-AND-SOCKET JOINTED TWO-PART THUMB PROSTHESIS

[75] Inventors: Yves Bouchon, Nancy; Hervé Dinville, Saint-Parres-aux-Tertres, both of France

[73] Assignee: Société dite JBS Société Anonyme, Troyes, France

[21] Appl. No.: 232,477

[22] Filed: Apr. 25, 1994

[30] Foreign Application Priority Data

Apr. 23, 1993 [FR] France .................................. 93 04921

[51] Int. Cl.$^6$ ...................................................... A61F 2/42
[52] U.S. Cl. ................... 623/21; 623/18; 606/62
[58] Field of Search ................... 623/18, 19, 20, 623/21, 22; 606/60, 62, 67

[56] References Cited

U.S. PATENT DOCUMENTS

| | | | |
|---|---|---|---|
| 4,180,871 | 1/1980 | Hamas | 623/21 |
| 4,944,758 | 7/1990 | Bekki et al. | 623/21 |
| 4,955,916 | 9/1990 | Carignan et al. | |
| 5,047,059 | 9/1991 | Saffar | 623/21 |
| 5,387,244 | 2/1995 | Breard | 623/18 |

FOREIGN PATENT DOCUMENTS

| | | |
|---|---|---|
| 0524874 | 1/1993 | European Pat. Off. . |
| 2670109 | 6/1992 | France . |
| 2424537 | 12/1974 | Germany . |
| 2049435 | 12/1980 | United Kingdom . |
| 2251795 | 7/1992 | United Kingdom . |

*Primary Examiner*—Paul B. Prebilic
*Attorney, Agent, or Firm*—Spencer & Frank

[57] ABSTRACT

A thumb prosthesis includes a trapezial component adapted to be fixed in the trapezium and a metacarpal component adapted to be fixed in the metacarpal bone. The trapezial component has a self-cutting thread adapted to be screwed into the trapezium; a polygonal base, having a conical surface and a neck part and being situated at one end of the self-cutting thread; and a spherical head disposed on the conical surface and extending from the neck part. The metacarpal component has a frustoconical head having a large-diameter end and an opposite, small-diameter end and a geometrical axis; a hemispherical socket provided in the small-diameter end and receiving a surface portion of the spherical head; and a stem extending from the large-diameter end of the frustoconical head. The stem is offset relative to the geometrical axis and has a decreasing triangular cross section with rounded corners as viewed in a direction away from the frustoconical head.

6 Claims, 3 Drawing Sheets

BALL-AND-SOCKET JOINTED TWO-PART THUMB PROSTHESIS

BACKGROUND OF THE INVENTION

The invention is in the field of prostheses and is more particularly directed to a rotating thumb prosthesis for replacement of the natural carpal joint.

It is well-known to apply surgical methods, first of all implanting joint prostheses for diminishing pains caused to patients by rheumatic inflammation. Finger joint reconstructions entailing prosthesis are primarily carried out on the carpo-metacarpal joint of the thumb.

Prior known prostheses for carpo-metacarpal joint replacement generally consist of two components. These two components of the artificial joint are the trapezine (proximal) component and the metacarpal (distal) component. The trapezine component of the prosthesis is made in most cases of a biocompatible plastic material which is fixed to the trapezial bone (trapezium) by asteointegration or bone cement. The metacarpal component is generally fixed in the first metacarpal bone by a metal stem.

A problem with these conventional prostheses is that the anchoring element supporting the actual prosthesis mechanism loosens and/or is damaged by the load during natural use. On the other hand, the movement with such prostheses is rather limited with respect to the natural joint motion.

In order to eliminate these problems it has been suggested to insert an elastic element made of biocompatible material between the trapezial component and the metacarpal component. Such type of prostheses is disclosed in the FR-PS 2 679 440. The prosthesis disclosed in this reference is provided with an intermediate element in the form of a piston which can freely reciprocate in a hole within metacarpal component. The piston like element is supported in the trapezial component of the prosthesis by a head which is fitted in a hemispherical cup arranged in the trapezial component of the prosthesis. The cup is made of a biocompatible material and is fixed to the trapezial component by bone cement.

The suggested prosthesis, however, has not eliminated the risk of loosening in the trapezium and the original freedom of the motion of the natural joint has not been reached. Furthermore, a new inconvenient effect has been brought with the new construction: the piston arranged in the hole of the metacarpal component makes a "pumping movement" due to the load on the head of the piston. This pumping effect produces different variations of pressure in the hole which cause pain during movement of the joint. Another consequence of the "pumping" is that detrimental dynamic effects are generated which act against the free reciprocating motion of the piston in the hole. Furthermore, there are necessarily dead spaces at the ends of the stroke of the piston and these dead spaces tend to collect organic materials which could decompose there and produce infections with serious consequences.

It is therefore the principal object of this invention to provide a prosthesis for eliminating these inconveniences.

SUMMARY OF THE INVENTION

Achievement of the foregoing object is made possible by the provision of a thumb prosthesis which on the one hand does not loosen either in the trapezium or in the metacarpal bone and furthermore enables angular motion of the thumb corresponding exactly to the natural motion of the joint and there is no need for applying an intermediate element.

The prosthesis according to the invention is comprises a first trapezial component provided with a spherical head to be fixed in the trapezium by osteointegration and a second, metacarpal component provided with a hemispherical cup to be fixed in the first metacarpal bone by bone cement, characterized in that the trapezial component provided with the spherical head and fixed in the muitangular bone of the wrist is provided with a self-cutting thread and a polygonal base carrying said spherical head wherein a conical surface and a neck part is arranged on the polygonal base. The metacarpal component provided with the hemispherical cup and fixed in the first metacarpal bone by a stem has a frustoconical head, the smaller end thereof including the hemispherical cup and the greater end thereof carrying the stem, said stem being shifted with respect to the geometrical axis of the conical head and having decreasing triangular cross-section with rounded corners.

According to a preferred embodiment, the cone angle of the conical surface of the first component is 150°.

According to another preferred embodiment, the cone angle of the conical head of the metacarpal component is 30° and there is a rounded circular edge between the surface of the hemispherical cup and the frustoconical head of the metacarpal component wherein the rounding of the edge has the same radius as that of the neck part between the spherical head and the conical surface in the polygonal base of the trapezial component.

The self cutting thread of the first component has preferably the cross-section of a rectangular triangle of 45°.

The advantages of the prosthesis according to the invention are as follows:

The two independent components of the prosthesis can easily and quickly be mounted in the respective bones by well-known surgical methods and devices and the metacarpal bone can be articulated completely with respect to the trapezium, due to the perfect anchorage of the components of the prosthesis.

These and other features and advantages of the present invention will become apparent from the following detailed description wherein references are made to the Figures in the accompanying drawing.

DESCRIPTION OF THE PREFERRED EMBODIMENT

Figure 1:
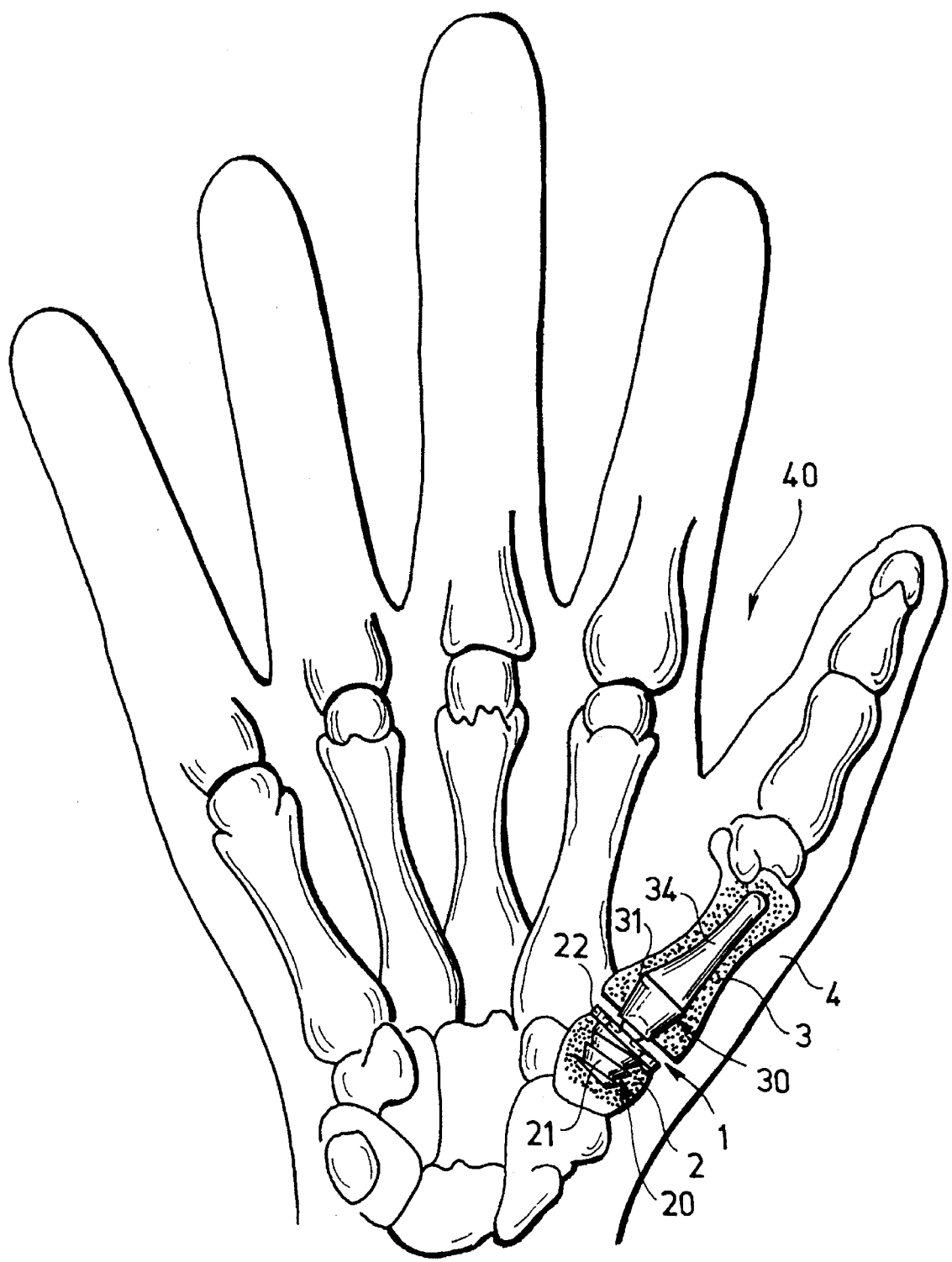
FIG. 1 is a perspective view of a preferred embodiment as mounted in a human hand in replacement of the natural carpo-metacarpal joint.

The prosthesis 1 according to the invention comprises a first, trapezial component 20 and a second, metacarpal component 30. The trapezial component 20 is fixed in the trapezium and the metacarpal component 30 is fixed in the first metacarpal bone of the thumb 4 of the hand 40. The trapezial component 20 is provided with an outer self-cutting thread 21 and a polygonal base 22 carrying a spherical head 23 wherein a rounded neck part 24 is between said spherical head 23 and a conical surface 25 of the polygonal base 22.

Figure 4:
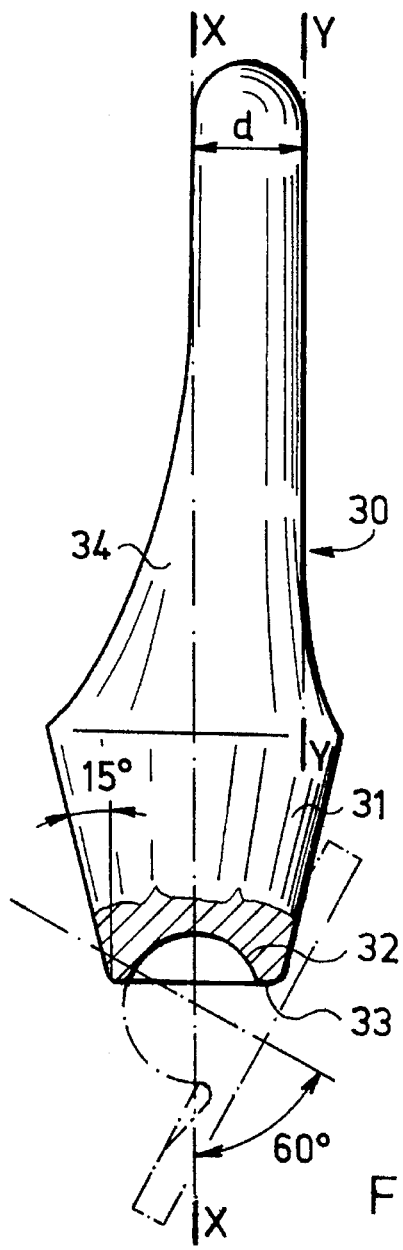
FIG. 4 is the side-view of the metacarpal component according to the invention, wherein the position of the trapezion component is also shown.
Figure 6:
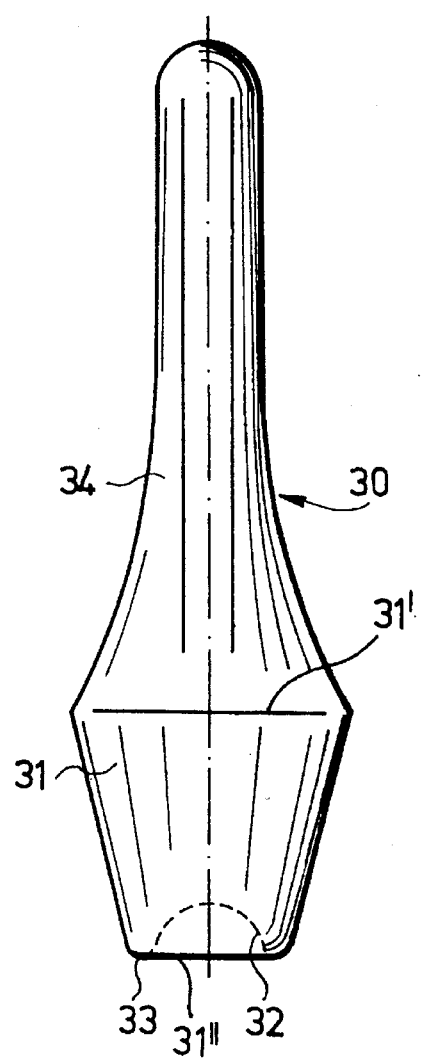
FIG. 6 is the front-view of the metacarpal component in FIG. 4.
Figure 5:
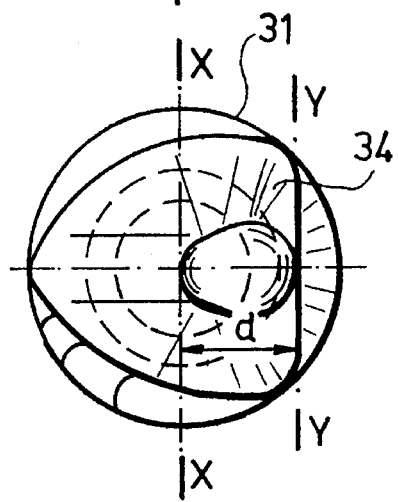
FIG. 5 is the top-view of the metacarpal component in FIG. 4.

The metacarpal component 30 comprises a frustoconical head 31 having a large-diameter end 31' and a small-diameter end 31". A hemispherical depression (socket) 32 is provided in the end 31". The depression 32 is bounded by a rounded annular ridge 33 whose radius is the same as that of the rounded neck part 24. A stem 34 for fixing the metacarpal component 30 is integrally connected to the frustoconical head 31 at the end 31' having the greater diameter. The stem 34 has a decreasing cross section and is shifted with respect to the geometrical axis of the frustoconical head 31. As may be seen upon considering FIGS. 4 and 5 together, the stem 34 has a progressively decreasing cross section as viewed in a direction away from the frustoconical head 31. The decreasing cross section of the stem 34 has the shape of an isosceles triangle the base of which is lying in the plane YY parallel with the geometrical axis XX of the frustoconical head 31, at a certain distance d therefrom. The sides of the triangle are outwardly bent.

Figure 2:
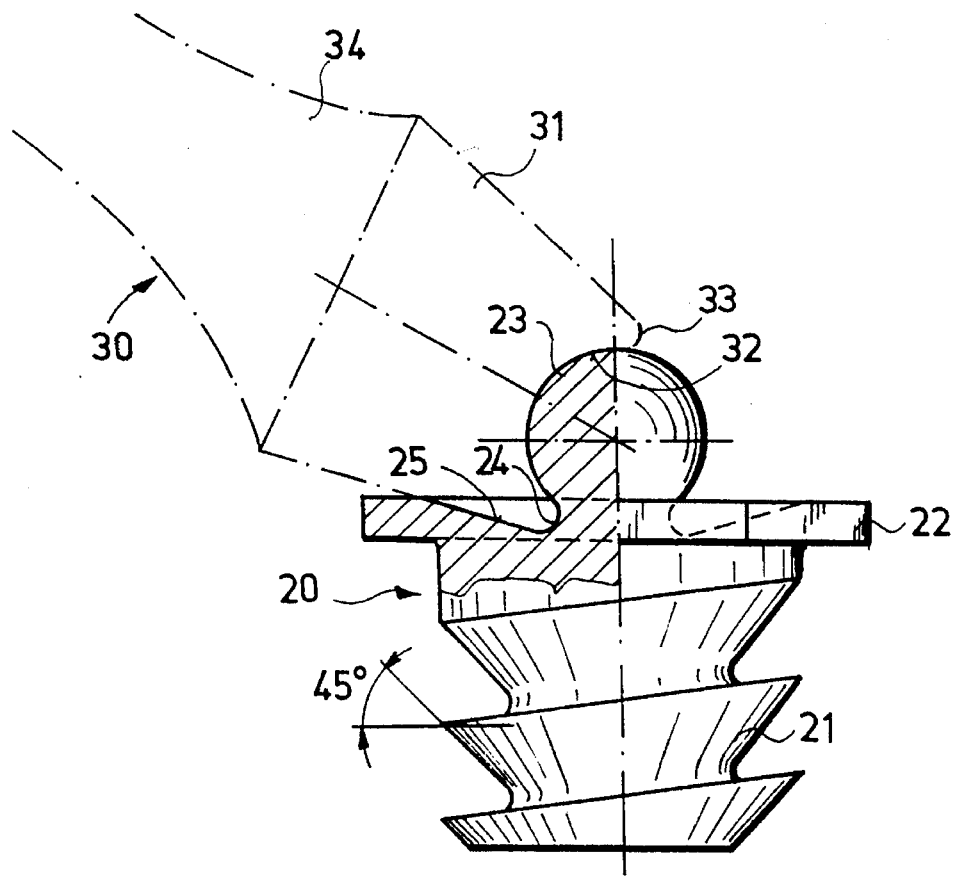
FIG. 2 is a side-view of the trapezial component of the prosthesis partly in cross-section, wherein the position of the metacarpal component is also shown.
Figure 3:
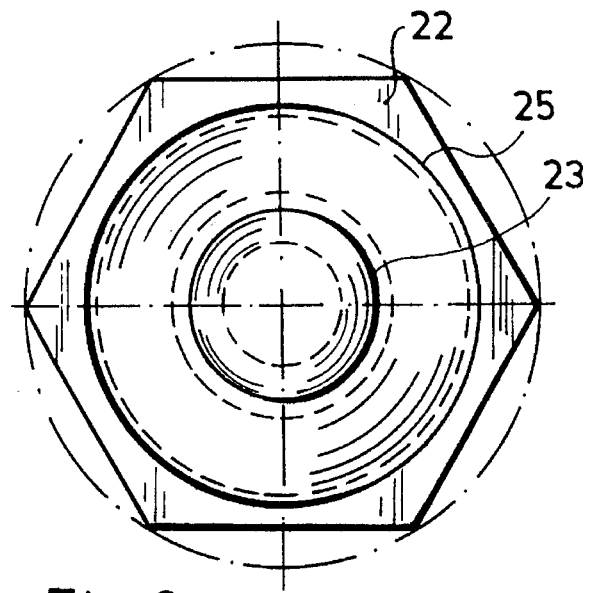
FIG. 3 is the top-view of the trapezial component in FIG. 2.

From FIGS. 1 to 3 it is clear that after having carried out a resection of a part of the trapezium, the trapezial component 20 of the prosthesis can be mounted in the trapezium by screwing self-cutting thread 21 in the inside of the trapezium by a spanner applied to the polygonal base 22 until said polygonal base 22 abuts on the surface of the trapezium 2.

After this first phase of mounting, stem 34 of the metacarpal component 30 is introduced into the first metacarpal bone 3 and the hemispherical cup 32 at the end of the frustoconical head 31 is brought in contact with the spherical head 23 of the trapazial component 20 of the prosthesis.

It is to be noted that the first metacarpal bone can be moved with respect to the trapezium in any direction at an angle of about 60°.

Of course, numeral other variations may obviously be made of the prosthesis herein described without departing from the present invention. Accordingly, the forms of the invention referred to in the Figures are illustrative only and are not intended to limit the scope of the invention defined by the following claims.

We claim:

1. A thumb prosthesis comprising
   (a) a trapezial component adapted to be fixed in the trapezium; said trapezial component including
      (1) a self-cutting thread adapted to be screwed into the trapezium;
      (2) a polygonal base situated at one end of said self-cutting thread; said polygonal base having a conical surface and a neck part; and
      (3) a spherical head disposed on said conical surface and extending from said neck part; and
   (b) a metacarpal component adapted to be fixed in the metacarpal bone; said metacarpal component including
      (1) a frustoconical head having a large-diameter end and an opposite, small-diameter end and a geometrical axis;
      (2) a hemispherical socket provided in said small-diameter end and receiving a surface portion of said spherical head; and
      (3) a stem extending from said large-diameter end of said frustoconical head; said stem being offset relative to said geometrical axis and having a decreasing triangular cross section with rounded corners as viewed in a direction away from said frustoconical head.

2. The thumb prosthesis as defined in claim 1, wherein said conical surface of said polygonal base has a cone angle of 150°.

3. The thumb prosthesis as defined in claim 1, wherein said frustoconical head has a cone angle of 30°.

4. The thumb prosthesis as defined in claim 1, wherein said hemispherical socket is bounded by a rounded annular ridge of said small-diameter end of said frustoconical head; said neck part of said polygonal base and said rounded annular ridge having the same radius.

5. The thumb prosthesis as defined in claim 1, wherein said triangular cross section has the shape of an isosceles triangle having a base and two outwardly bent sides; said base lying in a plane parallel with and spaced from said geometrical axis of said frustoconical head.

6. The thumb prosthesis as defined in claim 1, wherein said self-cutting thread has the cross-sectional shape of a rectangular triangle, one angle of which is 45°.

\* \* \* \* \*